(12) United States Patent
Iida et al.

(10) Patent No.: US 11,199,473 B2
(45) Date of Patent: Dec. 14, 2021

(54) OPTICAL PULSE TESTING DEVICE AND OPTICAL PULSE TESTING METHOD

(71) Applicant: NIPPON TELEGRAPH AND TELEPHONE CORPORATION, Tokyo (JP)

(72) Inventors: Hiroyuki Iida, Musashino (JP); Tetsuya Manabe, Musashino (JP); Yusuke Koshikiya, Musashino (JP); Hidenobu Hirota, Musashino (JP); Takui Uematsu, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 16/973,396

(22) PCT Filed: Jun. 4, 2019

(86) PCT No.: PCT/JP2019/022166
§ 371 (c)(1),
(2) Date: Dec. 8, 2020

(87) PCT Pub. No.: WO2019/239961
PCT Pub. Date: Dec. 19, 2019

(65) Prior Publication Data
US 2021/0239567 A1    Aug. 5, 2021

(30) Foreign Application Priority Data
Jun. 11, 2018    (JP) .............................. JP2018-110848

(51) Int. Cl.
*G01M 11/00* (2006.01)
*H04B 10/071* (2013.01)
*A61B 5/024* (2006.01)

(52) U.S. Cl.
CPC .... *G01M 11/3136* (2013.01); *G01M 11/3118* (2013.01); *H04B 10/071* (2013.01); *A61B 5/02444* (2013.01)

(58) Field of Classification Search
CPC . H04B 10/071; G01M 11/31; G01M 11/3109; G01M 11/3118; G01M 11/3127;
(Continued)

(56) References Cited

U.S. PATENT DOCUMENTS 4,875,772 A * 10/1989 Gentile .............. G01M 11/3136
356/73.1
5,067,810 A * 11/1991 Bu-Abbud ......... G01M 11/3136
356/73.1
(Continued)

FOREIGN PATENT DOCUMENTS

| JP | S62191733 A | 8/1987 |
| JP | 2000298077 A | 10/2000 |
| JP | 2011164075 A | 8/2011 |

*Primary Examiner* — Gordon J Stock, Jr.
(74) *Attorney, Agent, or Firm* — Harness, Dickey & Pierce, P.L.C.

(57) ABSTRACT

An object of the present invention is to provide an optical pulse test apparatus that can test an optical fiber cable at once in a short period of time. The optical pulse test apparatus according to the present invention includes: an optical pulse signal generation unit 11 that emits an optical pulse with a width that is n times as large as a pulse width T corresponding to desired spatial resolution; a light reception unit 12 that receives reflected light and back-scattered light from n FUTs; an optical path control unit 13 that switches paths connected to the n FUTs are connected at an interval T, inject the optical pulse, as a test optical pulse having the pulse width T, sequentially into the paths, then switches the paths at an interval ts that is shorter than the time period T, and emit the reflected light and the back-scattered light from the n FUTs sequentially onto the light
(Continued)

reception unit 12 at an interval n×ts; and an arithmetic processing unit 14 that divides the electrical signal output from the light reception unit 12, with an interval equal to the interval ts at which switching the paths is performed, into discrete signals respectively corresponding to the FUTs, and calculates the reflectance distributions of the reflected light and the back-scattered light of the respective FUTs.

8 Claims, 7 Drawing Sheets

(58) Field of Classification Search
CPC ......... G01M 11/3136; G01M 11/3145; G01M 11/3154; G01M 11/3163; G01M 11/3172; G01M 11/3181; G01M 11/319
See application file for complete search history.

(56) References Cited

U.S. PATENT DOCUMENTS

| | | | | |
|---|---|---|---|---|
| 5,090,802 A | * | 2/1992 | Longhurst | G01M 11/3154 356/73.1 |
| 5,137,351 A | * | 8/1992 | So | G01M 11/3154 356/73.1 |
| 5,396,569 A | * | 3/1995 | Yanagawa | G01M 11/3136 250/227.15 |
| 5,936,719 A | * | 8/1999 | Johnson | G01M 11/3136 356/73.1 |
| 5,995,687 A | * | 11/1999 | White | G01M 11/3136 385/14 |
| 6,028,661 A | * | 2/2000 | Minami | G01M 11/3136 356/73.1 |
| 6,141,466 A | * | 10/2000 | Shigehara | G01M 11/3127 372/50.11 |
| 6,310,702 B1 | * | 10/2001 | Minami | H04B 10/071 356/73 |
| 6,335,788 B1 | | 1/2002 | Uchiyama et al. | |
| 7,280,189 B2 | * | 10/2007 | Weller | G01N 21/00 356/73.1 |
| 8,325,330 B2 | * | 12/2012 | Hasegawa | G01M 11/3172 356/73.1 |
| 8,718,467 B2 | * | 5/2014 | Tsujimura | H04J 14/0295 398/16 |
| 8,928,868 B2 | * | 1/2015 | Takahashi | G01M 11/3109 356/73.1 |
| 9,900,087 B2 | * | 2/2018 | Ruchet | H04B 10/071 |
| 2011/0102776 A1 | * | 5/2011 | Hasegawa | G01M 11/3136 356/124.5 |
| 2021/0048369 A1 | * | 2/2021 | Noguchi | H04B 10/071 |

* cited by examiner

OPTICAL PULSE TESTING DEVICE AND OPTICAL PULSE TESTING METHOD

CROSS-REFERENCE TO RELATED APPLICATIONS

This application is a 371 U.S. National Phase of International Application No. PCT/JP2019/022166, filed on Jun. 4, 2019, which claims priority to Japanese Application No. 2018-110848 filed on Jun. 11, 2018. The entire disclosures of the above applications are incorporated herein by reference.

TECHNICAL FIELD

The present disclosure relates to an optical pulse test apparatus for measuring a light loss distribution, a breaking position, and the like of an optical line.

BACKGROUND ART

Optical Time Domain Reflectometry (hereinafter, referred to as OTDR) is a conventional technique for measuring a length, light loss distribution, and breaking position of an optical fiber under test (hereinafter, referred to as FUT). This OTDR is an apparatus that measures the reflectance distribution (hereinafter, referred to as an OTDR waveform) at each point on the FUT by injecting a test optical pulse into an FUT and measuring the power, in the time domain, of reflected light or Rayleigh back-scattered light (hereinafter, simply referred to as back-scattered light) generated with the test optical pulse in the FUT (see, for example, PTL1).

CITATION LIST

Patent Literature

PTL 1: JP 2011-164075 A

SUMMARY OF THE INVENTION

Technical Problem

Generally, when an optical fiber cable is constructed, laid, or repaired due to failure, all the optical fiber lines contained in the optical fiber cable are tested by the OTDR. Optical fiber cables could contain up to 2000 optical fiber lines, depending on the type of the cable. In principle, the OTDR is only capable of measuring the optical fiber lines one at a time. Thus, when a plurality of lines are measured by the OTDR, the lines to be measured need to be switched from one to another to be measured one by one. This means that the time required for the measuring a plurality of lines by the OTDR increases in proportion to the number of lines. Thus, there is a problem in that construction period for optical fiber cables is difficult to shorten.

In view of this, in order to solve the problems described above, an object of the present disclosure is to provide an optical pulse test apparatus and an optical pulse test method with which an optical fiber cable containing a large number of optical fiber lines can be tested at once within a short period of time.

Means for Solving the Problem

In order to solve the above problems, an optical pulse test apparatus according to the present disclosure receives return light sequentially from optical fiber lines at an interval shorter than a test optical pulse interval, and processes information about each of the optical fiber lines as discrete data.

Specifically, an optical pulse test apparatus according to the present disclosure is an optical pulse test apparatus that simultaneously measures reflectance distributions of reflected light and back-scattered light from n optical fibers, n being an integer equal to or larger than 2, the optical pulse test apparatus including:

an optical pulse signal generation unit that generates an optical pulse with a width that is n times as large as a pulse width T corresponding to desired spatial resolution;

a light reception unit that receives the reflected light and the back-scattered light from the n optical fibers, and output an electrical signal;

an optical path control unit that switches paths connected to the n optical fibers at an interval T, injects the optical pulse from the optical pulse signal generation unit, as a test optical pulse having the pulse width T, sequentially into the paths, then switches among the paths at an interval $t_s$ that is shorter than the time period T, and emit the reflected light and the back-scattered light from the n optical fibers sequentially onto the light reception unit at an interval $n \times t_s$; and an arithmetic processing unit that divides the electrical signal output from the light reception unit, with an interval equal to the interval $t_s$ at which the optical path control unit switches the paths, into discrete signals respectively corresponding to the n optical fibers, and calculates the reflectance distributions of the reflected light and the back-scattered light of the n respective optical fibers from the discrete signals.

An optical pulse test method according to the present disclosure is an optical pulse test method of simultaneously measuring reflectance distributions of reflected light and back-scattered light from n optical fibers, n being an integer equal to or larger than 2. This method includes emitting an optical pulse with a width that is n times as large as a pulse width T corresponding to desired spatial resolution; switching paths connected to n optical fibers at an interval T, injecting the emitted optical pulse, as a test optical pulse having the pulse width T, sequentially into the paths, then switching the paths at an interval $t_s$ that is shorter than the time period T, and emitting the reflected light and the back-scattered light from the n optical fibers sequentially onto a light reception unit at an interval $n \times t_s$; receiving, by the light reception unit, the reflected light and the back-scattered light from the n optical fibers and outputting an electrical signal; and dividing the electrical signal output from the light reception unit with an interval that is equal to the interval $t_s$ at which switching the paths is performed, into discrete signals respectively corresponding to the n optical fibers, and calculating the reflectance distributions of the reflected light and the back-scattered light of the n respective optical fibers from the discrete signals.

In the optical pulse test apparatus and method, the optical switch is used to input the test optical pulse sequentially into a plurality of FUTs, and then the optical switch is switched at an interval shorter than the test optical pulse to receive return light from the FUTs. Information about the return light from the FUTs is discrete rather than continuous. Still, with the switching interval of the optical switch set to be much shorter than the test optical pulse, failure to detect a reflection event in the FUTs can be prevented. Thus, a plurality of FUTs can be tested at once without compromising the test accuracy.

Thus, the present disclosure can provide an optical pulse test apparatus and an optical pulse test method with which an optical fiber cable containing a large number of optical fiber lines can be tested at once within a short period of time.

In the optical pulse test apparatus according to the present disclosure, the paths each include a dummy fiber that has a length enabling none of the reflected light and the back-scattered light from any of the n optical fibers to reach the optical path control unit while the optical path control unit performs switching at the interval T. Without the dummy fiber, the return light may be returned from the FUT to which the test optical pulse has already been injected, while the optical path control unit is still injecting the test optical pulse into the FUT. This may result in a failure to detect the information about the light. In the optical pulse test apparatus, the dummy fiber of the appropriate length is provided in the paths so that the failure to detect the information can be prevented.

In the optical pulse test apparatus according to the present disclosure, the optical pulse signal generation unit includes a continuous light generation unit and a light pulsing unit that pules the continuous light from the continuous light generation unit, and the light reception unit performs coherent detection on the reflected light and the back-scattered light from the n optical fibers by using the continuous light from the continuous light generation unit. In the optical pulse test apparatus, the coherent detection is performed to improve the measurement SN ratio.

In the optical pulse test apparatus according to the present disclosure, the optical pulse signal generation unit performs optical frequency encoding on the optical pulse at the interval T, and the optical path control unit sequentially injects the optical frequency encoded test optical pulse into the paths. Measurement efficiency of one covered optical fiber line can be increased in accordance with the frequency multiplexing count.

Effects of the Invention

The present disclosure can provide an optical pulse test apparatus and an optical pulse test method with which an optical fiber cable containing a large number of optical fiber lines can be tested at once within a short period of time.

DESCRIPTION OF EMBODIMENTS

Hereinafter, embodiments of the present disclosure will be described with reference to the drawings. The embodiments described below are examples of the present disclosure, and the present disclosure is not limited to the following embodiments. In this specification and the drawings, constituent elements having the same reference signs are assumed to be the same.

Embodiment 1

Figure 1:
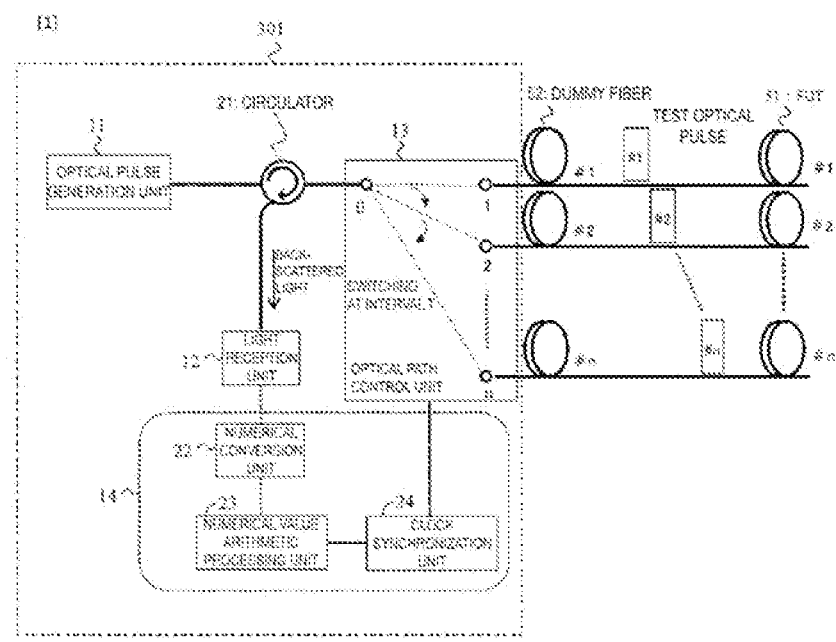
FIG. 1 is a diagram illustrating a configuration of an optical pulse test apparatus embodying the principles of the present invention.

FIG. 1 is a diagram illustrating a configuration of an optical pulse test apparatus 301 according to the present embodiment. The optical pulse test apparatus 301 is capable of collectively measuring reflectance distributions of reflected light and back-scattered light from n different FUT 51. The optical pulse test apparatus 301 includes:

an optical pulse signal generation unit 11 that emits an optical pulse with a width that is n times as large as a pulse width T corresponding to desired spatial resolution;

a light reception unit 12 that receives reflected light and back-scattered light from n FUTs 51, and outputs an electrical signal;

an optical path control unit 13 that switches paths connected to the n FUTs 51 at an interval T, inject the optical pulse from the optical pulse signal generation unit 11, as a test optical pulse having the pulse width T, sequentially into the paths, then switches the paths at an interval $t_s$ that is shorter than the time period T, and emits the reflected light and the back-scattered light from the n FUTs 51 sequentially onto the light reception unit 12 at an interval $n \times t_s$; and an arithmetic processing unit 14 that divides the electrical signal output from the light reception unit 12, with an interval equal to the interval $t_s$ at which the optical path control unit 13 performs switching, into discrete signals respectively corresponding to the n FUTs 51, and calculate reflectance distributions of the reflected light and the back-scattered light of the n respective FUTs 51 from the discrete signals.

The arithmetic processing unit 14 includes a numerical conversion unit 22, a numerical value arithmetic processing unit 23, and a clock synchronization unit 24.

Figure 2:
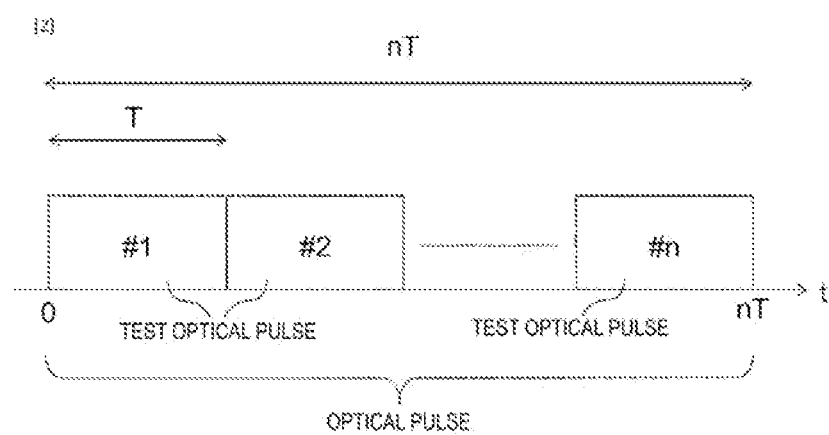
FIG. 2 is a diagram illustrating a time waveform of an optical pulse output from an optical pulse generation unit of the optical pulse test apparatus embodying the principles of the present invention.

FIG. 2 illustrates a time waveform of the optical pulses output from the optical pulse generation unit 11. The optical pulse generation unit 11 outputs an optical pulse with a length corresponding to a time width nT, where T represents the pulse width corresponding to spatial resolution of the measurement, and n represents the number of FUTs as illustrated in FIG. 2.

The optical pulse output passes through a circulator 21, and then is input to the optical path control unit 13. The optical path control unit 13 is an optical switch. The optical switch is driven at a speed with a switching width (described later) not exceeding $t_s$, to output input light sequentially to multiple ports. For example, the optical path control unit 13 is a semiconductor optical switch using a PLZT ((Pb, La)

(Zr, Ti) $O_3$) waveguide type optical switch or a semiconductor optical amplifier (SOA).

Figure 3:
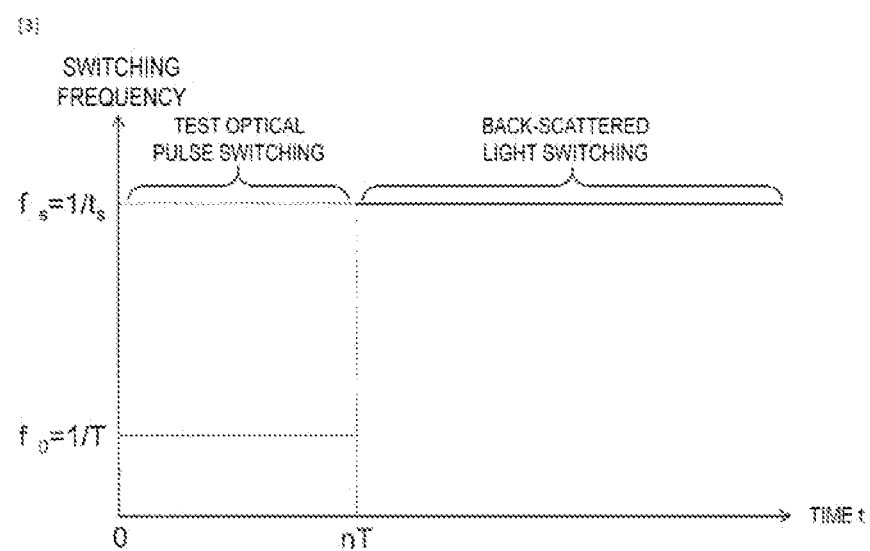
FIG. 3 is a diagram illustrating a temporal change in a switching frequency in path switching by an optical path control unit of the optical pulse test apparatus embodying the principles of the present invention.

FIG. 3 illustrates a temporal change in a switching frequency in path switching by the optical path control unit 13. During a period between time points 0 and nT, the optical pulse is divided by the pulse width T into n test optical pulses injected into the respective FUTs 51, and thus the switching frequency is the reciprocal of the pulse width T: $f_0=1/T$. On the other hand, the reflected light and the back-scattered light generated in each of the n FUTs 51 is received by the single light reception unit 12, and thus the switching frequency is the reciprocal of a switching time $t_s$ that is sufficiently smaller than the pulse width T: $f_s=1/t_s$.

The back-scattered light is generated immediately after the test optical pulse is injected into the FUT. Thus, direct connection of the FUT to an output port of the optical path control unit 13 may result in a failure to detect the reflection event of the back-scattered light from the FUT while the test optical pulse is being output to the output port at the switching frequency $f_0$ (between time points 0 and nT in FIG. 2). In view of this, a dummy fiber 52, adjusted to a length enabling the light to propagate in the fiber in the time width nT, is provided between the output port of the optical path control unit 13 and the FUT 51. In other words, between the output port of the optical path control unit 13 and the FUT 51, the dummy fiber is provided that has the length enabling none of the reflected light and the back-scattered light from any of then FUTs 51 to reach the optical path control unit 13 while the optical path control unit 13 is performing switching at an interval T.

With the optical path control unit 13 driven to switch the output ports 1, 2, . . . n at an interval of the pulse width T, the test optical pulse injected into the optical path control unit 13 is output as a pulse with the width T to the FUTs 1, 2, . . . , n, respectively. The test optical pulse with the pulse width T output from the optical path control unit 13 passes through the dummy fiber 52, and then is injected into the FUT 51. The back-scattered light generated respectively from the FUTs 51 #1, #2, . . . , and #n into which the test optical pulse has been injected passes through the dummy fiber 52, and then is input to the optical path control unit 13 driven with the switching width $t_s$ sufficiently smaller than the pulse width T. Here, the back-scattered light from each FUT 51 is continuous light, but due to the switching by the optical path control unit 13, the back-scattered light from one FUT 51 turns into beams of scatter light with the width $t_s$ and at an interval $T_s \times n$. Then, these beams of scattered light from the n FUTs appear as continuous light at an input port 0 of the optical path control unit 13.

The back-scattered light appearing at the input port 0 of the optical path control unit 13 passes through the circulator 21, and is then received by the light reception unit 12. The light reception unit 12 outputs an electrical signal to be sampled by the numerical conversion unit 22.

Figure 4:
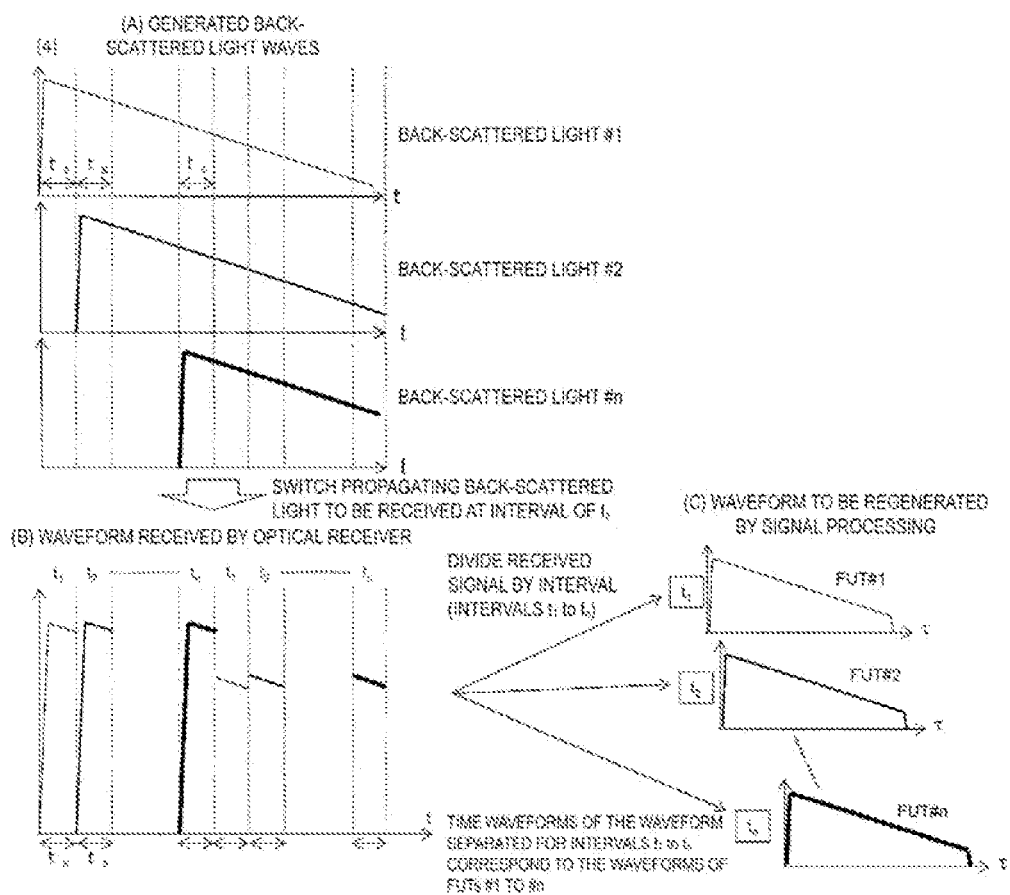
FIG. 4 illustrates a method of regenerating an OTDR waveform from FUTs, wherein the optical path control unit switches the back-scattered light generated from the FUTs at an interval $t_s$, a single light reception unit receives the back-scattered light, and then the reception signal is divided at the interval.

FIG. 4 illustrates a method of regenerating an OTDR waveform from the FUTs #1, #2, . . . , and #n, wherein the optical path control unit 13 switches the back-scattered light generated from the FUT 51 #1, #2, . . . , and #n at the interval $t_s$, the single light reception unit 12 receives the back-scattered light, and then the reception signal is divided at the interval $t_s$. FIG. 4(A) illustrates a time waveform of back-scattered light generated from each FUT 51. FIG. 4(B) illustrates a waveform of back-scattered light appearing at the input port 0 of the optical path control unit 13.

As illustrated in FIG. 4(B), the waveform of the back-scattered light received by the light reception unit 12 is characterized by the beams of the back-scattered light from the respective FUTs that are switched at the interval $t_s$. Thus, a numerical value arithmetic processing unit 23 uses the clock synchronization unit 24 to synchronize with the switching by the optical path control unit 13, to separate the reception signal received by the light reception unit 12 into n parts based on time intervals $t_1, t_2, \ldots$, and $t_n$. The numerical value arithmetic processing unit 23 repeatedly executes this separation processing entirely over the reception signal, and arranges the separated signals in the intervals $t_1, t_2, \ldots$, and $t_n$ along the time axis. Thus, the numerical value arithmetic processing unit 23 regenerates the OTDR waveform of the back-scattered light from the n FUTs 51 as discrete data.

Figure 5:
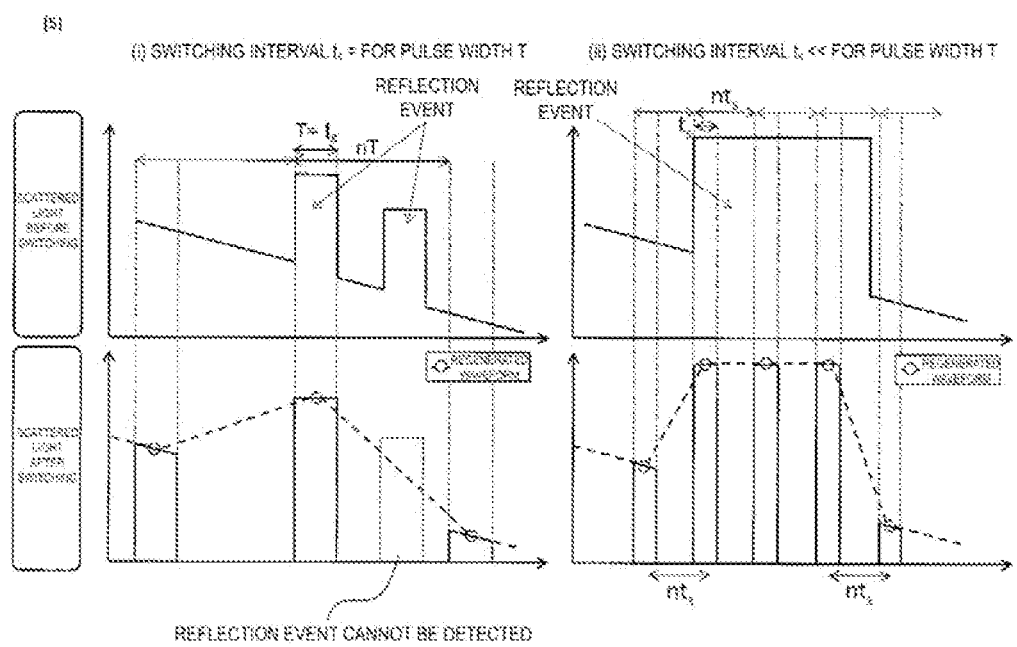
FIG. 5 illustrates a comparison of OTDR waveforms regenerated by the signal processing between Case (i) the switching interval $t_s$ and the pulse width T satisfy $t_s=T$ and Case (ii) $t_s$ and T satisfy $t_s \ll T$.

FIG. 5 illustrates a comparison of OTDR waveforms regenerated by the signal processing by the numerical value arithmetic processing unit 23 between Case (i) the switching interval $t_s$ and the pulse width T satisfy $t_s=T$ and Case (ii) $t_s$ and the pulse width T satisfy $t_s<T/20n$. As described above, in Case (i), regarding the OTDR waveform regenerated to be obtained by the signal processing, the spatial resolution may be deteriorated by n times. Furthermore, the reflection event may not be detectable. On the other hand, with the waveform regenerated by the signal processing in Case (ii), the reflection events can all be detected. Note that, since the spatial resolution deteriorates by up to $2nt_s$, n and the switching interval $t_s$ need to be set so that the $2nt_s$ does not exceed $1/10$ of the pulse width T, that is, so that $t_s<T/20n$ is satisfied.

Examples of specific numerical values are given below. The optical fiber cable to be measured is assumed to be a subsea cable, and the number n of lines is assumed to be 16. The required spatial resolution of the OTDR measurement of the subsea cable is 1 km. Thus, the pulse width T of the test optical pulse is assumed to be 10 µs. Note that the wavelength of the test optical pulse is assumed to be 1550 nm. Furthermore, a semiconductor optical switch enabling high-speed switching at an order of nanoseconds is used as the optical path control unit 13, and the switching interval $t_s$ is assumed to be 10 ns. With this configuration, the measurement speed can be increased by n=16 times. On the other hand, the OTDR waveform regenerated by the signal processing involves the reflection event having the time width increased by $2nt_s=320$ ns, and thus the spatial resolution deteriorates to be 1.032 km. Note that in this case, $2nt_s$ is approximately $1/31$ of the pulse width T.

Speed improvement with the spatial resolution at the same level as the conventional cases will be described. To achieve the spatial resolution that is equal to 1 km, the pulse width T of the OTDR is assumed to 9.7 µs for the pulse generation. In this case, the time width of the reflection event of the OTDR waveform regenerated by the signal processing is 10 µs, whereby the spatial resolution is maintained at 1 km. On the other hand, the change in the pulse width T from 10 µs to 9.7 µs results in degradation of the SN ratio of the OTDR measurement. With a method of increasing the number of signal measurement times (average time) adopted to compensate for the degradation of the SN ratio, the measurement time per line is increased by $(100/97)^2 \approx 1.06$ times. Thus, the measurement time of all of the 16 lines can be increased over that in the conventional method by $16/1.06 \approx 15.1$ times.

Embodiment 2

Figure 6:
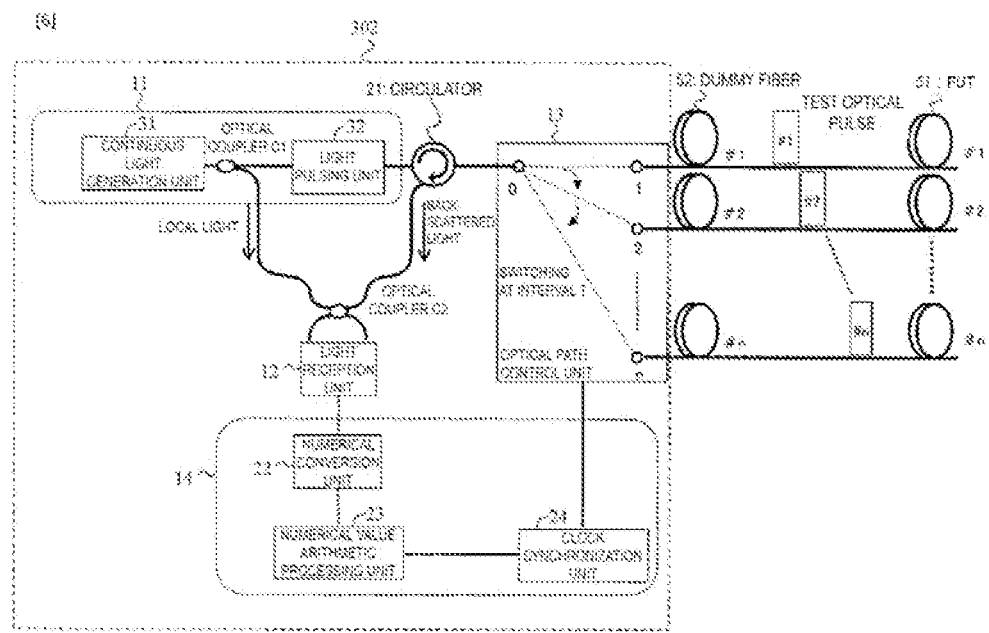
FIG. 6 is a diagram illustrating a configuration of the optical pulse test apparatus embodying the principles of the present invention.

FIG. 6 is a diagram illustrating a configuration of an optical pulse test apparatus 302 according to the present embodiment. The optical pulse test apparatus 302 is different from the optical pulse test apparatus 301 according to the first embodiment in that the optical pulse signal generation unit 11 includes a continuous light generation unit 31 and a light pulsing unit 32 that pules the continuous light from the continuous light generation unit 31, and in that the light reception unit 12 performs coherent detection on the reflected light and the back-scattered light from the n FUTs 51 by using the continuous light from the continuous light generation unit 31. The optical pulse test apparatus 302 employs a coherent detection scheme instead of the direct detection of the optical pulse test apparatus 301 according to the first embodiment.

The operation of the optical pulse test apparatus 302 will be described below with reference to FIG. 6.

Continuous light is required for the coherent detection. Thus, the optical pulse signal generation unit 11 of the optical pulse test apparatus 302 includes the continuous light generation unit 31 that generates continuous light and the light pulsing unit 32. The continuous light output from the continuous light generation unit 31 is split into two by an optical coupler C1, to have a part input to the light pulsing unit 32, and the other part serving as local light for the coherent detection. The light pulsing unit 32 generates a test optical pulse with the time width nT from the continuous light. The light pulsing unit 32 performs both of pulsing and frequency shifting of the light using, for example, an acoustic optical modulator (AOM). The test optical pulse is input to the optical path control unit 13 via the circulator 21.

Switching the test optical pulse at the interval T by the optical path control unit 13 and switching the back-scattered light at the switching interval $t_s$ are performed thereafter through the processing that is the same as that in the optical pulse test apparatus 301 described in the first embodiment. The back-scattered light output from the optical path control unit 13 passes through the optical circulator 21, then is combined with the local light described above in an optical coupler C2, and then is subjected to the coherent detection by the light reception unit 12. Beat signals of the local light and the back-scattered light output by the coherent detection are sampled as IF signals by the numerical conversion unit 22. Then, through mixing in the numerical value arithmetic processing unit 23, the IF signal is converted into a baseband signal, and the signal is further squared, whereby the power of the back-scattered light is converted into a numerical value as in the description of the first embodiment. The waveform regeneration processing for the back-scattered light from then FUTs 51 by the signal processing in the numerical value arithmetic processing unit 23 thereafter is the same as that described in the first embodiment.

The optical pulse test apparatus 302 receives light using the coherent detection scheme, and thus can improve the measurement SN ratio per pulse of the OTDR by about 20 dB compared with the optical pulse test apparatus 301 according to the first embodiment.

Embodiment 3

Figure 7:
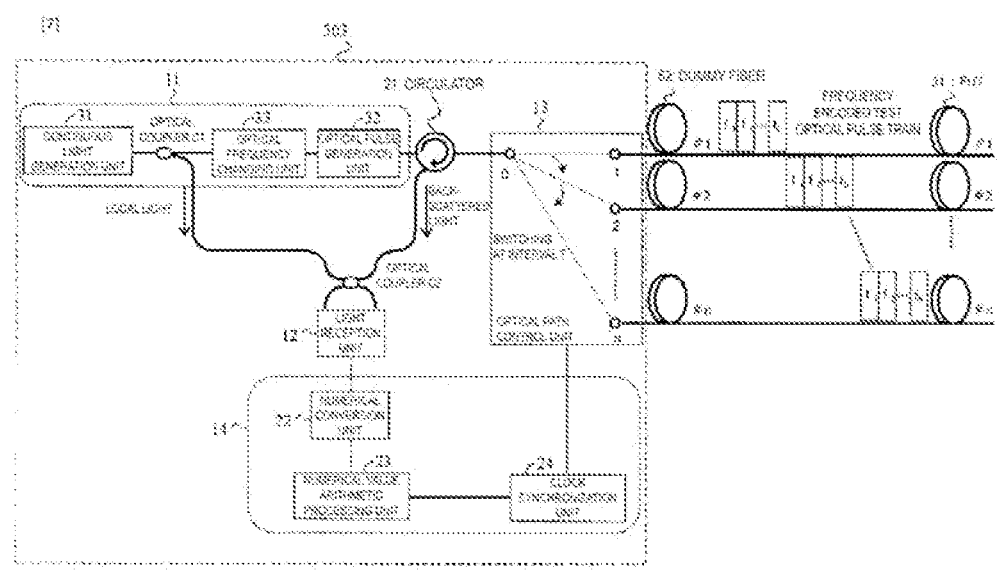
FIG. 7 is a diagram illustrating a configuration of the optical pulse test apparatus embodying the principles of the present invention.

FIG. 7 is a diagram illustrating a configuration of an optical pulse test apparatus 303 according to the present embodiment. The optical pulse test apparatus 303 is different from the optical pulse test apparatus 302 according to the second embodiment in that, the optical pulse signal generation unit 11 performs optical frequency encoding on the optical pulse once at the interval T, and in that the optical path control unit 13 sequentially injects the optical frequency encoded test optical pulses into the paths. The test optical pulse 303 performs coherent detection using a frequency encoded pulse train instead of the coherent detection by the optical pulse test apparatus 302 according to the second embodiment using a single frequency pulse.

The operation of the optical pulse test apparatus 303 will be described below with reference to FIG. 7.

To generate a frequency encoded optical pulse train, the optical pulse signal generation unit 11 of the optical test apparatus 303 further includes an optical frequency changing unit 33 provided in the optical pulse signal generation unit 11 of the optical pulse test apparatus 302. The continuous light output from the optical coupler C1 is input to the optical frequency changing unit 33. For example, the optical frequency changing unit 33 is a Single Side-Band (SSB) modulator. When the SSB modulator is driven while receiving each of sine waves at frequencies $f_1, f_2, \ldots,$ and $f_N$ for a time corresponding to the pulse width T, the SSB modulator outputs light waves with frequencies respectively shifted by $f_1, f_2, \ldots,$ and $f_N$.

These light waves are injected into the light pulsing unit 32 to be pulsed, thus the frequency encoded pulse train can be generated. As illustrated in FIG. 7, one test optical pulse (pulse width NT) has time-division multiplexed light waves with the optical frequencies $f_1, f_2, \ldots,$ and $f_N$ (one test optical pulse includes a frequency encoded pulse train). When n lines of FUTs are collectively measured, n pulses are generated as the frequency encoded test optical pulses. The optical path control unit 13 switches the FUTs at an interval of the time width NT of the frequency encoded pulse train.

Switching the back-scattered light at the switching interval $t_s$ and combining the back-scattered light with the local light for the coherent detection, as well as sampling their signals by the numerical conversion unit 22 are performed thereafter in the manner that is the same as those described in the second embodiment.

To execute frequency separation processing on the frequency multiplexed back-scattered light generated by the frequency coded pulse train, Fourier transform is performed on the beat signal received by the numerical value arithmetic processing unit 23. Then, N back-scattered light waves can be obtained by squaring each of the complex amplitudes of the frequencies $f_1, f_2, \ldots,$ and $f_N$ obtained by the Fourier transform.

Because the test optical pulse train having a plurality of frequencies is used, the optical pulse test apparatus 303 can measure the OTDR waveform of one line of the optical fiber N times faster than the optical pulse test apparatus 302 (measurement with a single frequency pulse), in accordance with the frequency multiplexing count (see PTL 1).

APPENDIX

The following describes an optical pulse test apparatus according to the present embodiment.

An optical pulse test apparatus that measures reflectance distributions of reflected light and back-scattered light from optical fibers, the optical pulse test apparatus including:
an optical pulse signal generation unit that emits a test optical pulse;
an optical path control unit that switches, for the test optical pulse, optical paths connected to respective test optical fibers at a predetermined interval;
an optical circulator that transmits the test optical pulse, and transmits back-scattered light toward a light reception unit, the back-scattered light being generated by reflection or scattering at each point in an optical fiber under test connected at a distal end of the optical path control unit;
the light reception unit that receives an optical signal from the optical circulator to acquire an electrical signal;

a numerical conversion unit that samples the electrical signal into digital signals; and an arithmetic processing unit that obtains the reflectance distributions of the reflected light and the back-scattered light from the optical fiber under test from the sampled signals, wherein the optical path control unit switches the optical paths respectively connected to the different test optical fibers at an interval shorter than a pulse width of the test optical pulse, the arithmetic processing unit divides sample data by an interval equal to the switching interval of the optical path control unit, and the back-scattered light from the different test optical fibers is simultaneously and collectively measured.

Effects of the Invention

The present disclosure can provide an optical pulse test apparatus and method that measures the reflectance distribution of an optical fiber cable with n lines, with efficiency improved by n times over conventional methods.

REFERENCE SIGNS LIST

11: Optical pulse generation unit
12: Light reception unit
13: Optical path control unit
14: Arithmetic processing unit
21: Optical Circulator
22: Numerical conversion unit
23: Numerical value arithmetic processing unit
24: Clock synchronization unit
31: Continuous light generation unit
32: Light pulsing unit
33: Optical frequency changing unit
51: FUT
52: Dummy fiber
301 to 303: Optical pulse test apparatus

The invention claimed is:

1. An optical pulse test apparatus operable to simultaneously measure reflectance distributions of reflected light and back-scattered light from n optical fibers, n being an integer equal to or larger than 2, the optical pulse test apparatus comprising:

an optical pulse signal generation unit configured to emit an optical pulse with a width that is n times as large as a pulse width T corresponding to desired spatial resolution;

a light reception unit configured to receive reflected light and back-scattered light from n optical fibers, and output an electrical signal;

an optical path control unit configured to switch paths connected to the n optical fibers at an interval T, inject the optical pulse from the optical pulse signal generation unit, as a test optical pulse having the pulse width T, sequentially into the paths, then switch the paths at an interval is that is shorter than the time period T, and emit the reflected light and the back-scattered light from the n optical fibers sequentially onto the light reception unit at an interval n×t$_s$; and an arithmetic processing unit configured to divide the electrical signal output from the light reception unit, with an interval equal to the interval is at which the optical path control unit performs switching, into discrete signals respectively corresponding to the n optical fibers, and calculate reflectance distributions of the reflected light and the back-scattered light of the n respective optical fibers from the discrete signals.

2. The optical pulse test apparatus according to claim 1, wherein the paths each include a dummy fiber that has a length enabling none of the reflected light and the back-scattered light from any of the n optical fibers to reach the optical path control unit while the optical path control unit performs switching at the interval T.

3. The optical pulse test apparatus according to claim 1, wherein the optical pulse signal generation unit includes a continuous light generation unit and a light pulsing unit configured to pulse the continuous light from the continuous light generation unit, and the light reception unit performs coherent detection on the reflected light and the back-scattered light from the n optical fibers by using the continuous light from the continuous light generation unit.

4. The optical pulse test apparatus according to claim 1, wherein the optical pulse signal generation unit performs optical frequency encoding on the optical pulse at the interval T, and the optical path control unit sequentially injects the optical frequency encoded test optical pulse into the paths.

5. An optical pulse test method of simultaneously measuring reflectance distributions of reflected light and back-scattered light from n optical fibers, n being an integer equal to or larger than 2, the method comprising:

emitting an optical pulse with a width that is n times as large as a pulse width T corresponding to desired spatial resolution;

switching paths connected to n optical fibers at an interval T, injecting the emitted optical pulse, as a test optical pulse having the pulse width T, sequentially into the paths, then switching the paths at an interval is that is shorter than the time period T, and emitting the reflected light and the back-scattered light from the n optical fibers sequentially onto a light reception unit at an interval n×t$_s$;

receiving, by the light reception unit, the reflected light and the back-scattered light from the n optical fibers and outputting an electrical signal; and dividing the electrical signal output from the light reception unit with an interval that is equal to the interval is at which switching the paths is performed, into discrete signals respectively corresponding to the n optical fibers, and calculating the reflectance distributions of the reflected light and the back-scattered light of the n respective optical fibers from the discrete signals.

6. The optical pulse test method according to claim 5, further comprising providing, to each of the paths, a dummy fiber that has a length enabling none of the reflected light and the back-scattered light from any of the n optical fibers to reach an optical path control unit performing the switching, during switching the paths at the interval T.

7. The optical pulse test method according to claim 5, wherein pulsing the continuous light from a continuous light generation unit is performed in emitting the optical pulse, and coherent detection on the reflected light and the back-scattered light from the n optical fibers is performed by using the continuous light from the continuous light generation unit in receiving the reflected light and the back-scattered light.

8. The optical pulse test method according to claim 5, wherein
   optical frequency encoding on the optical pulse at the interval T is performed in emitting the optical pulse, and
   sequentially injecting the optical frequency encoded test optical pulse into the paths is performed in switching the paths.

* * * * *